United States Patent [19]

Stephenson et al.

[11] Patent Number: 5,265,599
[45] Date of Patent: Nov. 30, 1993

[54] PATIENT TEMPERATURE CONTROL BLANKET WITH CONTROLLED AIR DISTRIBUTION

[75] Inventors: James G. Stephenson, Marshall; William F. Lohness, Jonesville; Eugene L. Kilbourn, Marshall, all of Mich.

[73] Assignee: Progressive Dynamics, Inc., Marshall, Mich.

[21] Appl. No.: 955,156

[22] Filed: Oct. 1, 1992

[51] Int. Cl.$^5$ ............................................. A61F 7/00
[52] U.S. Cl. ..................................... 607/104; 165/46; 5/423
[58] Field of Search ............... 128/399, 400, 402, 403, 128/376, 380; 165/46; 5/482, 423; 62/259.3; 4/160

[56] References Cited

U.S. PATENT DOCUMENTS

| | | | |
|---|---|---|---|
| 1,777,982 | 10/1930 | Popp | 128/376 |
| 2,093,834 | 9/1937 | Gaugler | |
| 2,110,022 | 3/1938 | Kliesrath | 5/423 |
| 2,512,559 | 6/1950 | Williams | 5/423 |
| 2,601,189 | 6/1952 | Wales, Jr. | 4/160 |
| 4,149,541 | 4/1979 | Gammons et al. | 128/400 |
| 4,572,188 | 2/1986 | Augustine et al. | 128/380 |
| 4,660,388 | 4/1987 | Greene | 165/46 |
| 4,777,802 | 10/1988 | Feher | 5/423 |
| 4,867,230 | 9/1989 | Voss | 165/46 |
| 5,044,364 | 9/1991 | Crowther | 128/400 |
| 5,106,373 | 4/1992 | Augustine et al. | 604/113 |
| 5,125,238 | 6/1992 | Ragan et al. | 62/259.3 |
| 5,165,400 | 11/1992 | Berke | 5/482 |

Primary Examiner—Mark S. Graham
Attorney, Agent, or Firm—Beaman & Beaman

[57] ABSTRACT

A disposal pneumatic temperature controlled blanket consisting of flexible upper and lower sheets interconnected at their peripheries to define an inflatable envelope. The lower sheet outer surface is provided with a friction producing layer and a plurality of orifices are formed in the lower sheet and layer whereby temperature controlled pressurized air introduced into the envelope will be distributed through the orifices upon the patient's body to regulate patient body temperature. The envelope sheets are staked or tacked intermediate the peripheries to control inflation and distribute the air and the location of the tacks define primary and secondary air passages to quickly and uniformly distribute the air with a minimum of heat loss to various blanket locations so as to achieve substantially uniform patient body temperature exposure.

9 Claims, 1 Drawing Sheet

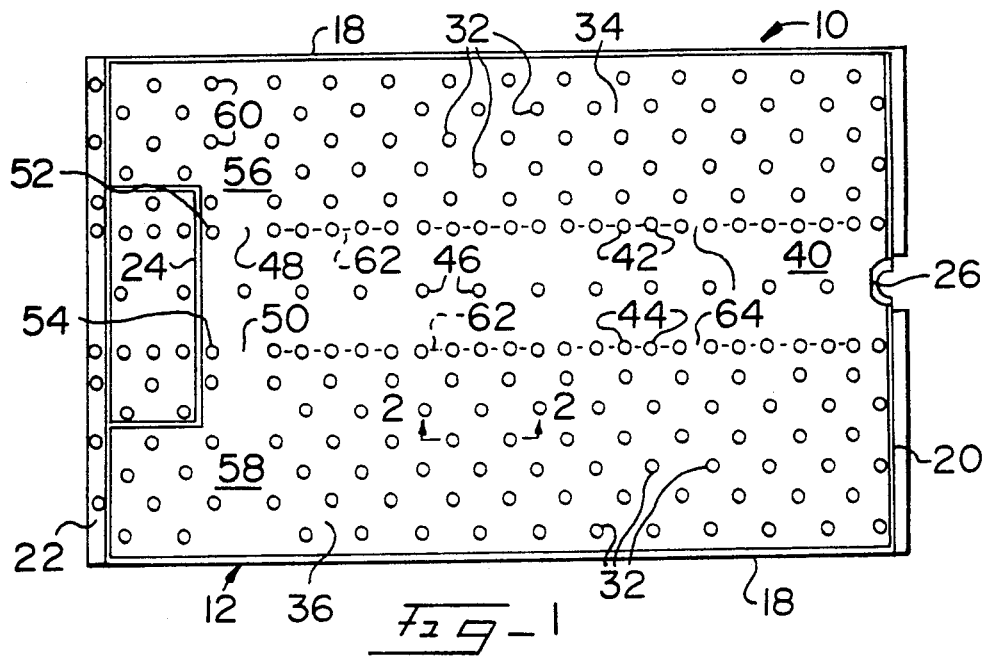
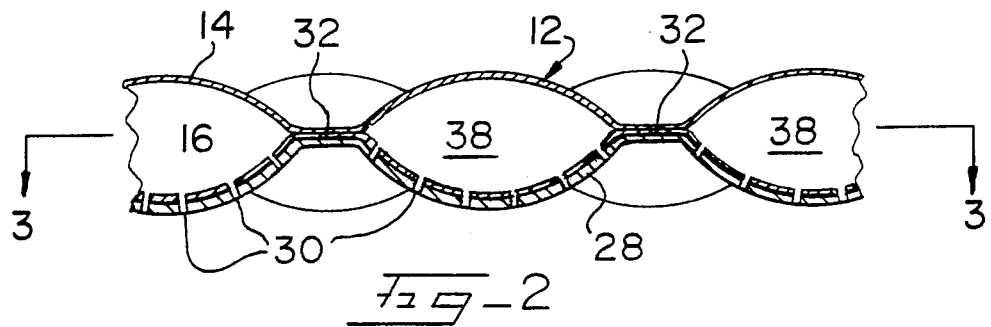
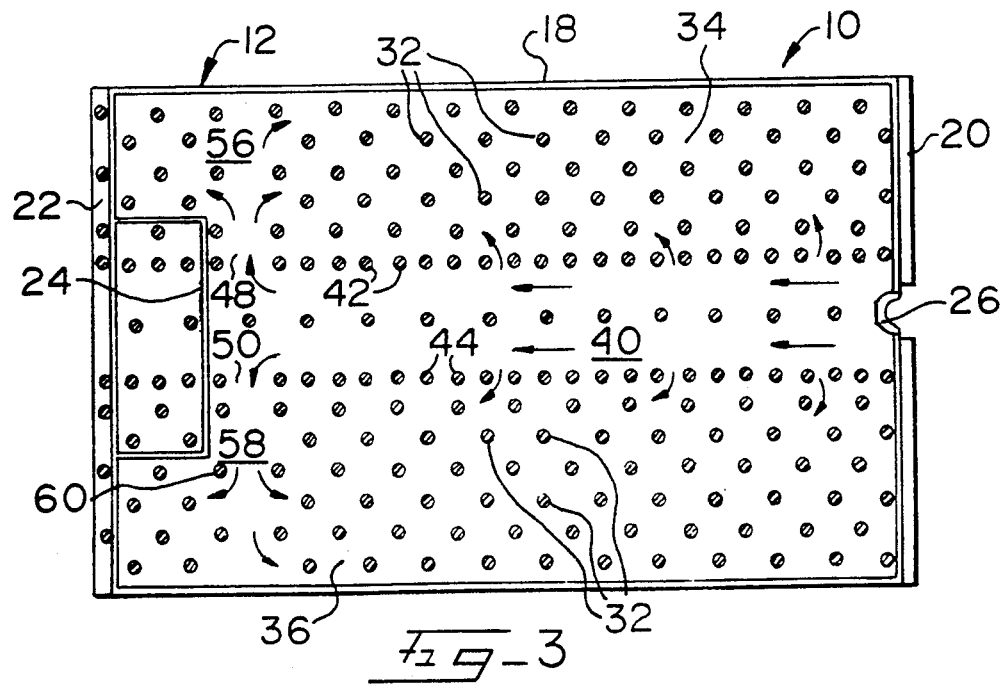

PATIENT TEMPERATURE CONTROL BLANKET WITH CONTROLLED AIR DISTRIBUTION

BACKGROUND OF THE INVENTION

As a patient's body temperature is critical with respect to sustaining life, thermal blankets are often used to provide warmth or cooling directly to patients as needed. For instance, many post-surgery procedures include the use of a thermal blanket wherein warm air is distributed over the patient's body for body temperature control purposes for reducing the effects of shock and trauma. As such blankets may become soiled, thermal blankets are preferably of the disposable type, the blanket being formed by thermoplastic sheets heat sealable at their peripheries to define an envelope for receiving pressurized air and orifices defined in the lowermost blanket sheet permits the warm air to be directed toward the patient's body.

FIELD OF THE INVENTION

The invention relates to patient warming or cooling blankets employing pressurized temperature controlled air wherein a substantially uniform temperature of air may be directly imposed over the entire area of a supine patient.

DESCRIPTION OF RELATED ART

Thermal blankets for controlling medical patients' body temperatures are shown in U.S. Pat. Nos. 2,093,834; 2,601,189; and 4,572,188. In these patents the blankets use elongated passages or cells for distributing the thermal medium over the area of the blanket. Manifolds may be used as shown in U.S. Pat. No. 2,601,189, or a plurality of longitudinally extending passages may be employed. Such devices are expensive to manufacture and are not suitable for disposable applications. Further, difficulty is experienced in providing substantially uniform temperatures throughout the area of the blanket.

Temperature controlled pads or blankets utilizing complex medium circulating paths are known as shown in U.S. Pat. No. 4,149,541, but again, such devices are complicated and expensive and not suitable for disposable body temperature regulating blankets.

In U.S. Pat. No. 4,867,230 a blanket warmer is shown of an envelope type wherein a plurality of air orifices are defined. The spacing of the orifices varies over the area of the blanket in order to provide a more uniform air distribution, i.e. the areas subject to the greatest positive pressure have the fewer orifices, but such an arrangement does not effectively control the distribution of the temperature of the air, and has the undesirable effect of subjecting portions of the patient's body to greater air velocities and quantities than other portions of the body.

In the assignee's U.S. Pat. No. 5,125,238, a patient warming or cooling blanket is shown wherein pressurized temperature controlled air is injected into a heat sealed envelope and orifices located in the bottom sheet of the envelope permit the air to impinge upon the patient's body. In this patent the envelope sheets are staked or tacked at evenly spaced locations to control inflation and provide a dissemination and distribution of the air entering the foot region of the blanket wherein the tacks partially define interconnected cells receiving the treated air. This type of blanket may be economically manufactured for producing a disposable single-use product. However, as the temperature controlled air enters the foot end of the blanket, sufficient heat loss has occurred as the air travels toward the head region of the blanket to prevent a uniform temperature air to be distributed throughout the blanket area.

OBJECTS OF THE INVENTION

It is a prime object of the present invention to provide a patient temperature control blanket utilizing pressurized air wherein an improved air path is produced within the blanket configuration by economical means to minimize heat loss as the air is distributed throughout the blanket resulting in a substantially uniform air temperature distribution over the blanket area.

Another object of the invention is to provide a temperature control blanket for distributing thermally regulated pressurized air over the body of a patient wherein the temperature of the distributed air is substantially uniform, and the manufacturing techniques used are of such an economical nature as to permit the blanket to be economically produced for disposable single-use applications.

A further object of the invention is to provide a temperature control blanket for medical use formed of thermoplastic sheets heat sealed at their peripheries and staked, welded or tacked by heat sealing procedures intermediate the blanket periphery to control inflation and provide air flow passages and paths which reduce temperature differentiation throughout the blanket area and permit a substantially uniform temperature of air to be distributed over the patient.

Yet another object of the invention is to provide a pneumatic temperature control blanket which produces an even, low pressure distribution of temperature controlled air over the covered area regardless of where the blanket air chamber may be compressed by superimposed blankets or the like.

SUMMARY OF THE INVENTION

In the practice of the invention a disposable pneumatic temperature control blanket is formed by sealing thermoplastic sheets about their peripheries to define a closed envelope. Preferably, at least one of the sheet's exterior surfaces includes a layer of friction material to aid in the retention of the blanket upon the patient's body. An external air supply unit provides a low pressure heated or dehumidified and cooled air through a flexible hose, and the conditioned air is introduced into the blanket chamber through a blanket mounted fitting.

The sheets defining the blanket envelope are staked or tacked by a heat weld at spaced locations between the sheets' peripheries, and such tacking provides a diffused air flow passage throughout the envelope and aids in preventing the envelope from being compressed at localized regions such as to interfere with the flow of air therethrough.

The location and spacing of predetermined tacks is such that a low flow restrictive air passage is defined within the blanket envelope in communication with the air supply connection fitting whereby air introduced into the envelope readily flows through the blanket throughout its length to permit rapid dissemination of the air throughout the entire blanket area. Preferably, the air supply is connected to the blanket adjacent the blanket rear end, and the air flows through the air passage toward the blanket head end through the air passage.

The air passage within the blanket envelope may be formed by spaced individual tacks, or an interrupted seam. By using spaced tacks, even though the tacks are relatively close to each other, the air may escape laterally from the air passage into the lateral blanket portions throughout the length of the air passage. Further, adjacent the blanket head end auxiliary lateral air passages are defined by the spacing of tacks to permit low restrictive air flow into lateral regions of the blanket adjacent the head and shoulder region of the blanket as disposed over a patient.

By the use of the internal air passages, air flow characteristics within the blanket envelope are improved over prior art arrangements, including that shown in U.S. Pat. No. 5,125,238, and a substantially uniform temperature of air can be distributed and discharged over the blanket area and over the patient's body. Yet, the use of the thermally sealed tacks permits the blanket to be economically manufactured and feasibly producible for disposable single-use applications.

BRIEF DESCRIPTION OF THE DRAWINGS

The aforementioned objects and advantages of the invention will be appreciated from the following description and accompanying drawings wherein:

FIG. 1 is a plan view of a temperature control blanket utilizing the concepts of the invention, an alternative air passage seam construction being illustrated in dotted lines, FIG. 2 is an elevational, enlarged, sectional view of the inflated blanket as taken along Section 2—2 of FIG. 1, and FIG. 3 is a plan sectional view through the inflated blanket as taken along Section 3—3 of FIG. 2, the air flow through the passages being represented by arrows.

DESCRIPTION OF THE PREFERRED EMBODIMENT

The pneumatic temperature control blanket 10 in accord with the invention is preferably of a rectangular configuration as will be appreciated from FIGS. 1 and 3. Basically, the blanket consists of an envelope 12 defined by a pair of polyethylene thermoplastic sheets 14 and 16, the sheet 14 constituting a top sheet, while the sheet 16 forms the blanket bottom sheet. The sheets 14 and 16 are heat sealed along their lateral edges 18, and along their foot edges 20 and head end edges 22.

The head edges 22 are heat sealed at 24 to define a non-inflatable region adjacent the neck, and at the foot edges 20 a fitting 26 is affixed to the blanket envelope for receiving an air supply hose, not shown, for providing pressurized temperature controlled air to the blanket. A non-woven wood pulp airlaid layer 28 is bonded to the outside of the lower sheet 16 forming the lower surface of the blanket 10, and the layer 28 forms a high friction surface which retains the blanket upon the wearer.

A plurality of air orifices 30 extend through the sheet 16 and the layer 28 whereby air within the envelope 12 passes through the orifices 30 onto the patient's body located below the blanket. Preferably, the orifices 30 are formed in accord with the disclosure of Ser. No. 07/915,254 filed Jul. 20, 1992.

The above disclosure with respect to the general construction of blanket 10, including fitting 26, is identical to that disclosed in the assignee's U.S. Pat. No. 5,125,238, and the disclosure of this patent is herein incorporated by reference. Preferably, the fitting 26 is identical to the hose fitting disclosed in U.S. Pat. No. 5,125,238, and the operation of the blanket, and use with the patient, of the instant invention is identical to that disclosed with respect to U.S. Pat. No. 5,125,238.

As disclosed in U.S. Pat. No. 5,125,238 the envelope sheets 14 and 16 are staked or tacked together by a plurality of heat sealed tacks 32 which interconnect the associated sheets and control the expansion of the envelope 12 during inflation with pressurized air. At the blanket lateral regions 34 and 36, the tacks 32 are uniformly spaced from each other, and as will be appreciated from FIG. 2, upon inflation of the envelope 12 the air chambers 38 defined by adjacent tacks 32 are in communication with each other and air freely flows between the chambers 38 for flow through the orifices 30.

In order to reduce the resistance of the air flow into the envelope 12 an elongated air passage 40 is defined by tacks 42 and 44. The tacks 42 define a linear row extending from the foot edges 20 toward the head edge 22, and the spacing between adjacent tacks 42 is relatively close, as will be appreciated from FIGS. 1 and 3, and is closer than the spacing between the tacks 32 defined in the blanket lateral edges. Likewise, the tacks 44 are located within a linear row identical to tacks 42 extending from the foot edge of the blanket toward the head edge. The close proximity of the tacks 42 and 44 to each other, respectively, defines the air passage 40 and permits lateral dissemination of air within the passage 40 to the lateral regions 34 and 36 as shown by the arrows, FIG. 3. However, due to the proximity of the tacks 42 and 44 to each other, respectively, lateral flow of the air from the passage 40 is limited.

Center tacks 46 are located within the air passage 40 in a linear configuration defining a longitudinal axis of the air passage 40, and the center tacks 46 prevent excessive separation of the sheets 14 and 16 within the passage 40, without significantly restricting the passage of air therethrough.

As will be readily appreciated from FIGS. 1 and 3, the air supply fitting 26 communicates with the foot end of the air passage 40.

At its head end the air passage 40 is provided with ports 48 and 50 defined within the air passage 40 adjacent the envelope head end and head heat seal 24. The ports 48 and 50 are defined by a significant separation between the last of the tacks 42 and 44 in their respective rows, and the tacks 52 and 54.

Lateral air passages 56 and 58 formed by a significant spacing between tacks 32 and tacks 60 communicate with the ports 48 and 50, respectively. In this manner the air flowing through air passage 40 encounters heat seal 24 and laterally passes through ports 48 and 50 into passages 56 and 58 whereby the air passing through the ports is effectively distributed in the lateral regions 34 and 36 of the blanket which are adjacent the shoulder and chest blanket regions. Also, air flowing through the passages 56 and 58 will flow through the chambers 38 defined by the tacks 32 in the blanket lateral regions and distribute air through the lateral regions.

The inflation of the blanket 10, and the air flow through the passage 40, will cause the temperature controlled air, usually heated, to flow laterally between the tacks 42 and 44, and also through the ports 48 and 50, and through the lateral passages 56 and 58 as shown by the arrows, FIG. 3. As the air flow through the passage 40 is relatively non-restrictive, the temperature of the air within the lateral passages 56 and 58 will be substantially equal to that received within the air passage 40 adjacent the fitting 26, and by the use of the larger air passages 40, 56 and 58 a substantially uniform temperature of air throughout the entire area of the blanket 10 is achieved, permitting relatively uniform air to be dispensed over the patient throughout the patient's height.

As will be appreciated from the drawings, the width of the blanket lateral regions 34 and 36 slightly differs, and this dimensional difference is due to manufacturing techniques and permits proper location of the blanket upon the patient. It is to be appreciated that orifices 30 are also located within the portions of the sheet 16 defining the air passage 40, and passages 56 and 58 whereby the flow of air from the blanket will be substantially uniform throughout its entire area.

It is to be appreciated that the tacks 42 and 44 defining the air passage 40 may not necessarily be separately defined, but may constitute short continuous seams 62 as shown in dotted lines in FIG. 1, rather than spot welds. With such a modification the seams 62 would be interrupted to define lateral orifices as at 64 to permit air to be laterally distributed into the regions 34 and 36 as occurs when using the spot tacks 42 and 44.

It is appreciated that various modifications to the inventive concepts may be apparent to those skilled in the art without departing from the spirit and scope of the invention.

We claim:

1. A pneumatic temperature control blanket receiving air through an external pressurized air supply connection wherein the blanket comprises an envelope formed by first and second sheets sealed together at their peripheries, the blanket having a longitudinal axis, a central region, lateral regions, a head end and a foot end, a plurality of air dispensing orifices defined in at least one of the sheets and the sheets being interconnected within the sheet's peripheries by spaced tacks, the improvement comprising, closely spaced first tacks being so positioned as to define a primary reduced flow resistance air passage within the blanket envelope in communication with the air supply connection and defining lateral ports within said air passage establishing communication between said air passage and the remainder of the envelope interior including the lateral regions, the lateral regions including second tacks, the spacing between adjacent second tacks being greater than the spacing between adjacent first tacks.

2. In a pneumatic temperature control blanket as in claim 1, said first tacks being located in first and second spaced rows, each of said rows being substantially linear and substantially parallel to the blanket axis and said rows being located upon opposite sides of the blanket axis whereby said air passage is parallel to and symmetrically related to the blanket axis.

3. In a pneumatic temperature control blanket as in claim 1, said first tacks being located in first and second spaced rows, each of said rows being substantially linear and substantially parallel to the blanket axis, said rows extending between the blanket's head and foot ends whereby said primary air passage extends between the blanket head and foot ends, the air supply connection communicating with said air passage adjacent the blanket foot end.

4. In a pneumatic temperature control blanket as in claim 3, wherein large reduced flow resistance ports are located within said air passage adjacent the blanket head end.

5. In a pneumatic temperature control blanket as in claim 4, a plurality of third tacks defining lateral air passages within the envelope, said lateral air passages being in communication with said primary air passage at said reduced flow resistance ports.

6. In a pneumatic temperature control blanket as in claim 5, said lateral air passages being located adjacent the blanket head end.

7. In a pneumatic temperature control blanket as in claim 1, said first tacks comprising a continuous seam interconnecting the first and second sheets.

8. In a pneumatic temperature control blanket as in claim 7, said first tacks being located in first and second spaced seams, each of said seams being substantially linear and substantially parallel to the blanket axis and said seams being located upon opposite sides of the blanket axis whereby said air passage is parallel to and symmetrically related to the blanket axis.

9. In a pneumatic temperature control blanket as in claim 7, said first tacks being located in first and second spaced seams, each of said seams being substantially linear and substantially parallel to the blanket axis, said seams extending between the blanket's head and foot ends whereby the primary air passage extends between the blanket head and foot ends, the air supply connection communicating with said air passage adjacent the blanket foot end.

* * * * *